United States Patent [19]

Matsuda et al.

[11] 4,180,795
[45] Dec. 25, 1979

[54] ALARM DEVICE FOR INFORMING REDUCTION OF PNEUMATIC PRESSURE OF TIRE

[75] Inventors: Akira Matsuda, Higashi-Murayama; Makoto Tanaka; Junichi Murata, both of Kodaira; Shigeo Yasuda; Hiroshi Nishino, both of Musashino, all of Japan

[73] Assignees: Bridgestone Tire Company, Limited, Tokyo; Mitaka Instrument Company Limited, Musashino, both of Japan

[21] Appl. No.: 859,517

[22] Filed: Dec. 12, 1977

[30] Foreign Application Priority Data

Dec. 14, 1976 [JP] Japan .................................. 51-150235

[51] Int. Cl.² .......................................... B60C 23/02
[52] U.S. Cl. .................................. 340/58; 200/61.25
[58] Field of Search ............ 340/58; 200/61.22, 61.25

[56] References Cited

U.S. PATENT DOCUMENTS

| | | | |
|---|---|---|---|
| 3,602,884 | 8/1971 | Brumbelow | 340/58 |
| 4,064,482 | 12/1977 | Maisch et al. | 340/58 |

Primary Examiner—Alvin H. Waring
Attorney, Agent, or Firm—Sughrue, Rothwell, Mion, Zinn and Macpeak

[57] ABSTRACT

An alarm device for informing reduction of pneumatic pressure of vehicle tires by sensing abnormal change of tire internal pressure of a vehicle when running by a pressure sensing switch, by converting the thus sensed abnormal change into an electric signal and by generating an alarm to an operator. This device comprises an oscillator having an oscillation coil fixed on a chassis side of the vehicle; a resonator consisting of a resonance coil and a capacitor fixed to a peripheral portion of the rotating wheel having tire adjacent the oscillation coil and for resonating with an electromagnetic wave radiated from the oscillation coil; a signal processing device containing a sensing means for sensing change in an oscillation condition generated in the oscillator due to a resonant condition of the resonator switched on and off in accordance with abnormal internal pressure of a tire and for processing a signal sensed by this sensing means; and an alarm for generating a warning by the output of this signal processing device.

5 Claims, 12 Drawing Figures

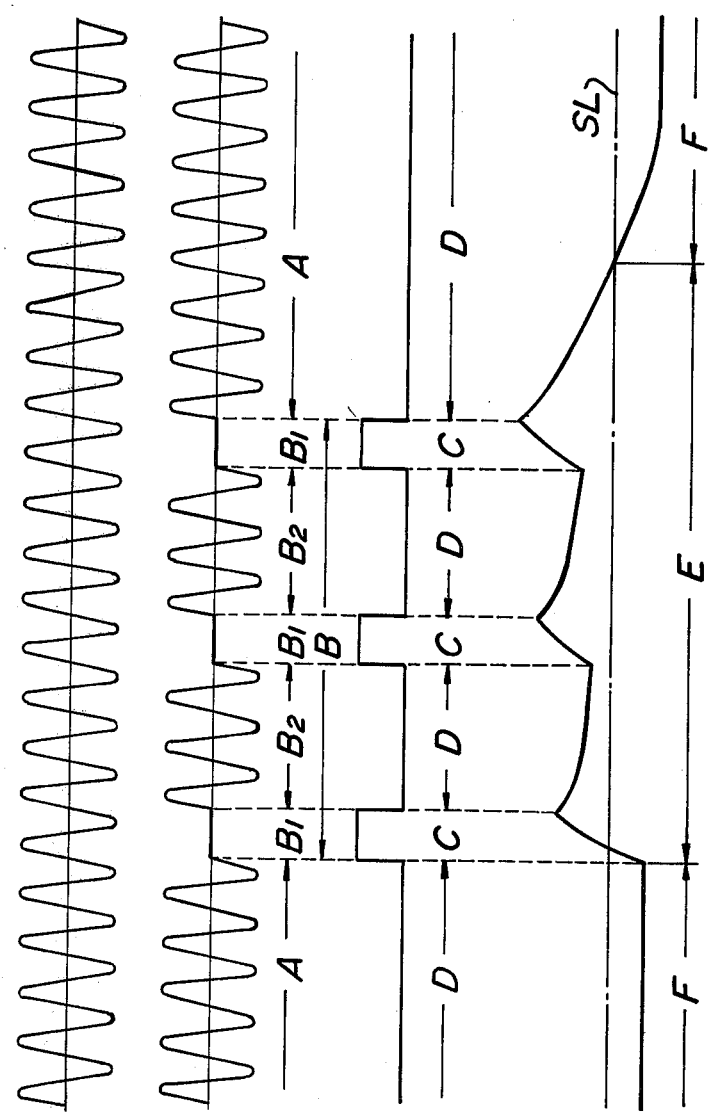

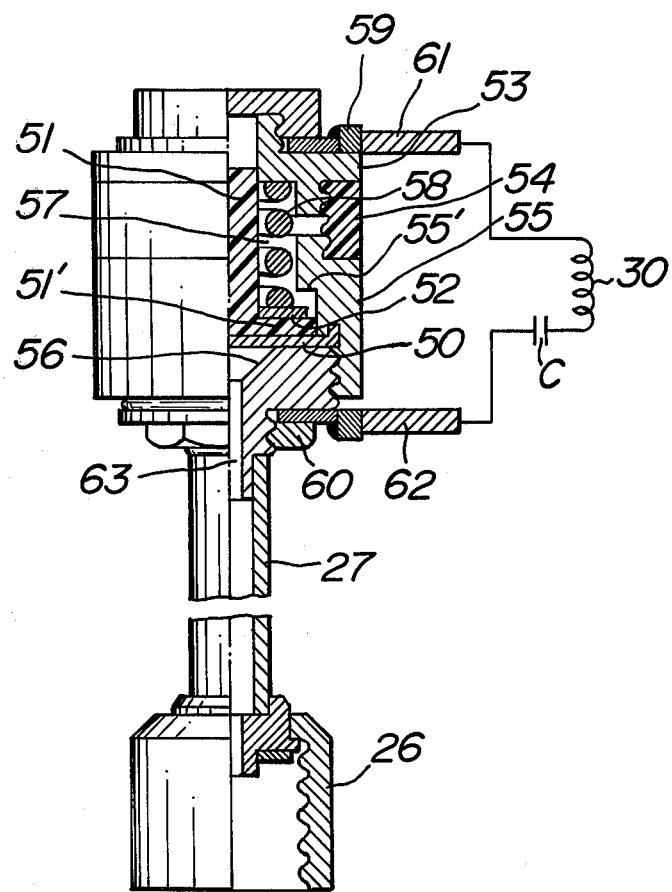

4,180,795

ALARM DEVICE FOR INFORMING REDUCTION OF PNEUMATIC PRESSURE OF TIRE

BACKGROUND OF THE INVENTION

1. Field of the Invention

The present invention relates to an alarm device for informing reduction of pneumatic pressure of vehicle tires by sensing abnormal change of tire internal pressure of a vehicle when running and by informing it to an operator.

2. Description of the Prior Art

An alarm device for informing an alarm to an operator by sensing abnormal change caused by reduced pressure of internal pressure of a tire in a vehicle, such as a puncture and the like, is well known by for example U.S. Pat. No. 3,810,090. Such device comprises a transmitter having an oscillator for generating a high frequency signal by sensing change of tire internal pressure and a transmitter antenna for radiating an electromagnetic wave by its output, a receiver having a receiver antenna attached on the chassis side of a vehicle for receiving the electromagnetic wave from the transmitter antenna and for processing the electromagnetic wave received by this antenna, and an alarm for generating a warning to an operator.

This kind of devices, however, is liable to be misoperated by receiving an influence of noises from a spark plug generated by a vehicle itself and noises from the outside and lacks reliability. In order to construct a device for receiving no influence of such noises, its mechanism becomes complicated and as a result, the device becomes expensive and impracticable.

SUMMARY OF THE INVENTION

An object of the present invention is to provide an alarm device for informing reduction of pneumatic pressure of a tire, which is simple in construction, light in weight and easy in production.

Another object of the present invention is to provide an alarm device for informing reduction of pneumatic pressure of a tire, which is cheap, reliable and practicable.

The alarm device for informing reduction of pneumatic pressure of a tire according to the present invention senses abnormal change of tire internal pressure of a vehicle by a pressure sensing switch, converts such abnormal change into an electric signal and generates an alarm to an operator. The device comprises an oscillator having an oscillation coil fixed on a chassis side of the vehicle; a resonator consisting of a resonance coil and a capacitor fixed to a peripheral portion of the rotating wheel having a tire adjacent the oscillation coil and for resonating with an electromagnetic wave radiated from the oscillation coil; a signal processing device containing a sensing means for sensing change in an oscillation condition generated in the oscillator due to a resonant condition of the resonator switched on and off in accordance with abnormal internal pressure of a tire and for processing a signal sensed by this sensing means; and an alarm for generating a warning by the output of this signal processing device.

BRIEF DESCRIPTION OF THE DRAWINGS

FIG. 3 is a waveform showing the oscillation state of an oscillator of the device according to the invention;

FIG. 4 is a waveform showing the oscillation state of the oscillator in case of receiving an influence of the resonator;

FIG. 5 is a waveform showing the output of a comparator of the device according to the invention;

FIG. 6 is a waveform showing the output of an integrator of the device according to the invention;

FIG. 12 is a partial cross-sectional view showing the pressure sensing switch and the resonator of the resonance section at abnormal tire internal pressure.

DESCRIPTION OF THE PREFERRED EMBODIMENT

Figure 1:
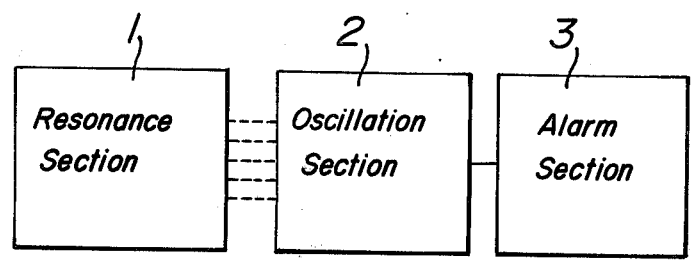
FIG. 1 is a block diagram showing the principle of an alarm device for informing reduction of pneumatic pressure of tire according to the invention.
Figure 2:
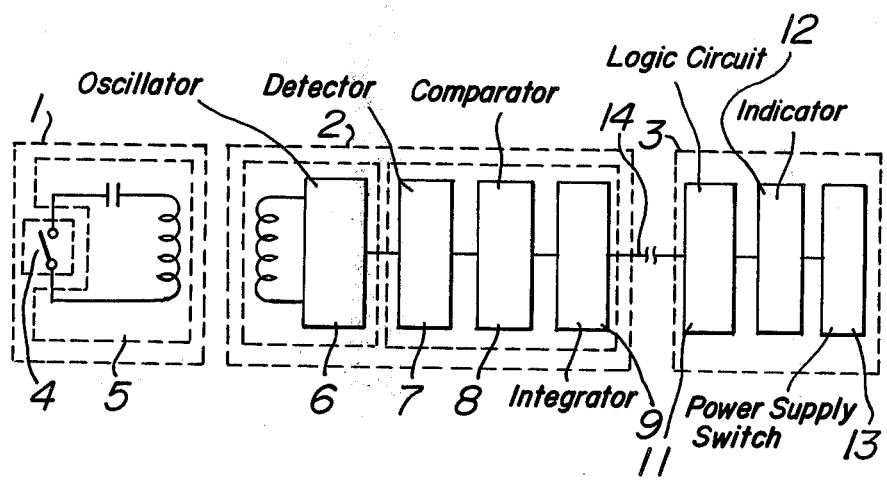
FIG. 2 is a block diagram showing the construction of the device according to the invention.

Referring to FIG. 1, a principal structure of the alarm device for informing reduction of pneumatic pressure of tire according to the invention is shown. The device comprises a resonance section 1, an oscillation section 2 and an alarm section 3. As shown in FIG. 2, the resonance section 1 comprises a pneumatic pressure sensing switch 4 for a change of tire internal pressure of a vehicle and a resonator 5 consisting of a series combination of a resonance coil and a capacitor. The switch 4 and the resonator 5 are integrally formed and rotatably mounted on each wheel of a vehicle as stated hereinafter. The oscillation section 2 comprises an oscillator 6 consisting of a series or parallel circuit of an oscillation coil and a capacitor, and a signal processing device 10 including a detector 7 for detecting the output of the oscillator 6, a comparator 8 for comparing the output of the detector 7 with a reference signal and an integrator 9 for integrating the output of the comparator 8. The oscillator 6 and the signal processing device 10 are mounted at the portion opposed to the chassis adjacent the resonance section 1. In this case, a preferable distance between the resonator 5 and the oscillator 6 is 5-40 mm, preferably 10-30 mm. An preferable oscillation frequency of the oscillator 6 is 20 KHz-10 MHz, preferably 100 KHz-5 MHz. The alarm section 3 comprises a logic circuit 11 for logically operating the output of the integrator 9, an indicator 12 for indicating the output of the circuit 11 and a power supply switch 13. The alarm section 3 is connected to the integrator 9 of the signal processing device 10 through a cable 14 and mounted on a dashboard of the vehicle.

Operation of the alarm device for informing reduction of pneumatic pressure of tire according to the invention will be explained with reference to FIGS. 3-6. The pneumatic pressure sensing switch 4 of the resonance section 1 shown in FIG. 2 senses change of tire internal pressure, particularly reduction of pneumatic pressure, closes during normal internal pressure and opens during abnormal internal pressure thereby to make the resonator 5 switch on or off. The construction of the pressure sensing switch 4 will be explained in greater detail hereinafter. The resonator 5 becomes in a resonating condition under the switched on state of the pressure sensing switch 4 during normal internal pressure and becomes in a non resonating condition under the switched off state of the pressure sensing switch 4 during abnormal internal pressure, i.e., reduced pressure state. FIG. 3 shows a waveform of an oscillating current which exhibits the oscillation condition of the oscillator 6 of the oscillation section 2. FIG. 4 shows the state that the oscillating current of the oscillator 6 of the oscillation section 2 has an amplitude changed by approach of the resonator 5 provided on the wheel side. In FIG. 4, a waveform A shows the state that the resonator 5 is open-circuited by reduction of the tire internal pressure when running and that the oscillator 6 is not influenced by the resonator 5 when the resonator 5 and the oscillator 6 are at positions separated from each other. That is, the resonator 5 has no influence on the oscillator 6 under such a state. A waveform B shows the state that the oscillation current of the oscillator 6 is changed by influence of the resonator 5 under the resonatable state when the tire internal pressure is normal while running.

In the section B of FIG. 4, a section $B_1$ shows a waveform when the resonator 5 fixed to the wheel approaches the oscillator 6 by rotation. That is, in this section $B_1$, if the resonator 5 approaches the oscillator 6, oscillation energy is absorbed in the resonator 5, so that the current in the oscillator becomes abnormal and amplitude of the oscillation current becomes almost zero. A section $B_2$ shows a waveform when the resonator 5 is separated from the oscillator 6. That is, in the section $B_2$, the oscillator 6 does not receive any influence from the resonator 5 so that the oscillation current has again original amplitude. Accordingly, the waveforms shown in the sections $B_1$ and $B_2$ correspond to the case when a signal having a certain amplitude is subjected to amplitude modulation.

The output of the oscillator 6 for generating the waveform shown in FIG. 4 is detected by the detector 7 of the signal processing device 10 and a voltage value of a certain amplitude (corresponding to sections A and $B_2$ shown in FIG. 4) and a voltage value of the modulated amplitude (corresponding to section $B_1$ shown in FIG. 4) are compared with each other in the comparator 8. The output of the comparator 8 is shown in FIG. 5. A section D shown in FIG. 5 corresponds to the sections A and $B_2$ shown in FIG. 4, and a section C shown in FIG. 5 corresponds to the section $B_1$ shown in FIG. 4. The comparator 8 is so constructed that it generates a pulse when a changed amount of an amplitude between the sections $B_1$ and $B_2$ becomes more than a certain level and generates no pulse when the amplitude difference between the sections A and $B_2$ and the sections $B_1$ becomes less than a certain level. In other words, the comparator compares successive outputs from the detector and provides pulses whenever a sufficient difference is present between successive detector outputs. If amplitude modulation does not occur, due to the opening of switch 4, the detector outputs will all be the same and no pulses will be supplied by the comparator 8.

The waveform shown in FIG. 5, i.e., the output of the comparator 8 is integrated by the integrator 9 of the signal processing device 10 and a waveform shown in FIG. 6 is obtained. That is, the integrator 9 starts integral operation by the leading edge of a pulse in the section C shown in FIG. 5 and completes the integral operation by the trailing edge. Therefore, pulses shown in FIG. 5 are continuously generated during normal running, so that the output of the integrator 9 becomes an integral waveform shown by a section E shown in FIG. 6 and finally saturated, but during abnormal running, i.e., when the tire internal pressure is lowered and the vehicle is stopped, there are waveforms of attenuation amplitude less than a predetermined level SL shown in a section F shown in FIG. 6 and zero amplitude.

When internal pressure of a tire becomes lower than the predetermined value for some reason or other during running of vehicle, the pressure sensing switch 4 of the resonance section 1 becomes the off state and the resonator 5 cannot be operated, the oscillator 6 generates a continuous oscillation signal as shown in the section A of FIG. 4, so that the output of the comparator 8 becomes zero amplitude as shown in the section D of FIG. 5; namely, no pulse is generated and as a result, the waveform shown in the section F of FIG. 6 has an amplitude attenuated to less than the predetermined level SL or zero amplitude. When the amplitude becomes less than the predetermined level SL the output of the integrator is detected by the logic circuit 11 and an alarm is generated from the indicator 12. When this indicator 12 is of an indicating lamp, the lighting of the lamp informs to an operator of vehicle that internal pressure of the tire is reduced to less than the predetermined value. In this case, as an indicating means, color indication can also be used in a manner such that the indicating lamp shows a blue color when neumatic pressure is normal and a red color when the pressure is abnormal.

A relation between the above described predetermined level SL and a discharge time constant of the integrator is so determined that a discharge characteristic curve of the integrator shown in FIG. 6 becomes not more than the predetermined level SL at low speed running, for instance a speed of 10 km/h.

There is shown means of securing the alarm device for informing reduction of pneumatic pressure of tire according to the invention as follows.

Figure 7:
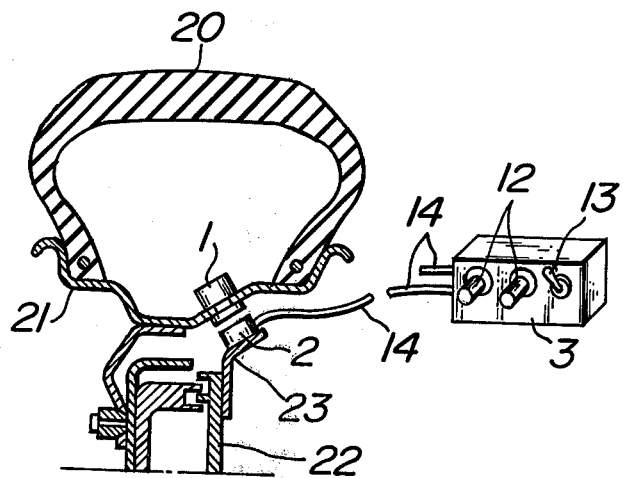
FIG. 7 shows cross-sectional view showing an embodiment of the device according to the invention, in which the resonant portion is fixed to a rim inclined portion of the wheel.

FIG. 7 shows means of securing the resonance section 1 of the alarm device according to the invention to a peripheral portion of a wheel, for instance a recessed inclining portion of a rim 21 for supporting a tire 20. In this embodiment, the oscillation section 2 is secured to a bracket 23 of a chassis 22 at the position opposed to the inclined portion of the rim. This oscillation section 2 is connected to the alarm section 3 through the cable 14. The alarm portion 3 is mounted to for instance a dashboard at the driver's seat.

Figure 8:
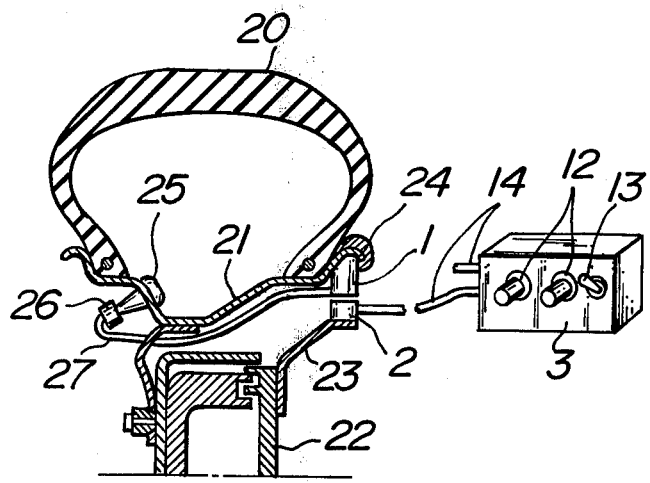
FIG. 8 is a cross-sectional view showing another embodiment of the device according to the invention in which the same resonant portion is fixed to a rim flange portion of the wheel.

FIG. 8 shows means of securing the resonance section 1 of the alarm device according to the invention to a rim flange portion 24 of the wheel. In FIG. 8 like parts of the component shown in FIG. 7 are denoted with like numerals. In this embodiment, the resonance section 1 is secured to the flange portion 24 of the rim 21, so that a valve 25 is communicated with the pressure sensing switch 4 of the resonance section 1 through a cap nut 26 screwed to the valve 25 and an air pipe 27.

Figure 9:
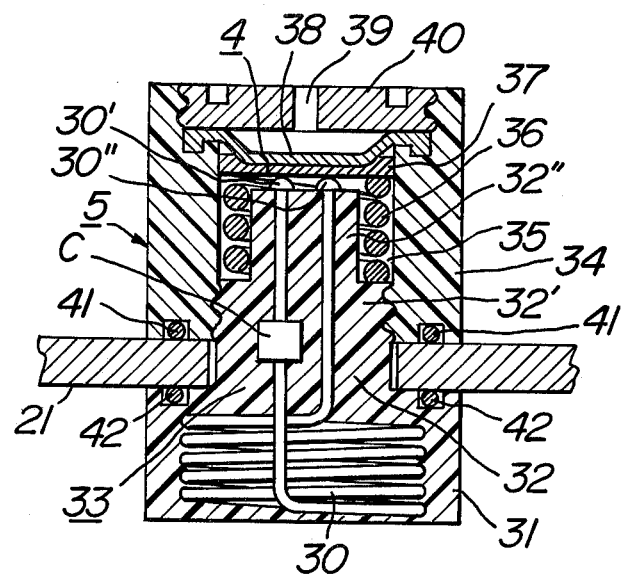
FIG. 9 is a cross-sectional view showing a construction of the resonance section consisting of a pressure sensing switch and a resonator integrally formed at normal tire internal pressure in detail.
Figure 10:
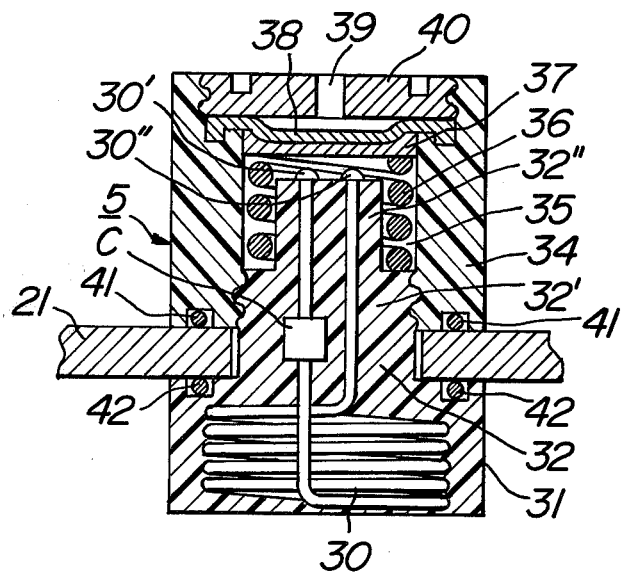
FIG. 10 is a cross-sectional view showing a construction of the resonator at abnormal tire internal pressure.

FIGS. 9 and 10 show the states that the resonator 5 becomes in an operating condition and an inoperating condition by switching on and off of the pressure sensing switch 4 of the resonance section 1 shown in FIG. 7 in accordance with internal pressure of the tire.

FIG. 9 shows the case that the internal pressure of the tire 20 is normal and the pressure sensing switch 4 is closed. In this embodiment, the resonance section 1 comprises a resin molded body 33 having a rim flange portion 31 and a screw threaded step column 32, sealed a resonance coil 30 and a capacitor C therein, a cylindrical threaded spring case 34 threadedly mounted on a large threaded column portion 32', spring 36 provided in a spring chamber 35 formed between the cylindrical spring case 34 and a small column portion 32" of the resin molded body 33, a metal switch plate 37 engaged with a free end of the spring 36 and made into contact with coil ends 30', 30" projected to the end surface of the small column portion 32", a bellofram 38 for compressing the metal switch plate 37 to the coil ends 30', 30" against force of the spring 36 when the internal pressure of the tire is normal, and a bellofram press plate 40 having an air path 39 at the center and screwed into the cylindrical spring case 34. That is, the pressure sensing switch 4 of the resonance section 1 shown in FIG. 2 comprises the bellofram 38, the metal switch plate 37 and the spring 36. In case of securing such resonance section 1 to a wheel, the rim flange portion 31 and the cylindrical spring case 34 are fixed to the rim 21 of the wheel through two O-rings 41, 42. The step column 32 is inserted into a hole bored at the inclined portion of the rim 21 through the O-rings 41, 42 and the screw of the cylindrical spring case 34 is threaded into the screw portion of the step column 32 from the inside of the tire 30 and sealed. The spring 36 is inserted into the spring chamber 35 formed between the small column portion 32" and the cylindrical spring case 34 and the metal switch plate 37 and bellofram 38 are placed on the free end of the spring. The bellofram 38 is fixedly secured by screwing the bellofram press plate 40 into the end portion of the cylindrical spring case 34 thereby securing the periphery of the bellofram 38 to the cylindrical spring case 34.

When the internal pressure of the tire is normal, the bellofram 38 is pressed to the end portion of the small column portion 32" against force of the spring 36 by internal pressure of the tire 20 through the air path 39 at the center of the bellofram press plate 40, so that the ends 30' and 30" of the resonance coil are short-circuited by the metal switch plate 37.

When the internal pressure of the tire is abnormal, i.e., the internal pressure of the tire is reduced, however, the bellofram 38 and the metal switch plate 37 are pushed back in the direction of the bellofram press plate 40 by force of the spring 36 as shown in FIG. 10, so that the coil ends 30', 30" are separated from the metal switch plate 37 and as a result, the resonator 5 becomes in an inoperating condition.

Figure 11:
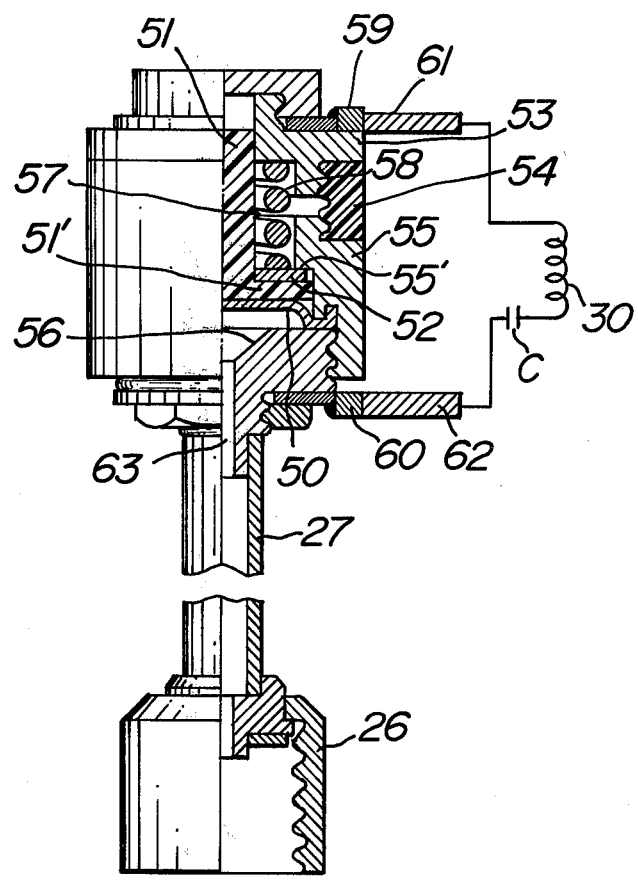
FIG. 11 is a partial cross-sectional view showing another construction of the pressure sensing switch and the resonator of the resonance section at the normal tire internal pressure.

FIGS. 11 and 12 show the construction of the pressure sensing switch 4 of the resonance section 1 when the resonance section 1 is secured to the rim flange portion 24 as shown in FIG. 8.

FIG. 11 shows the construction of the pressure sensing switch 4 when the internal pressure of the tire 20 is normal. In this embodiment, the pressure sensing switch comprises a bellofram 50, a piston 51 and a contact ring 52. A cylinder portion of the piston 51 is formed by threading a metal spring press member 53, an insulating ring 54, a metal case 55 and a bellofram press member 56 with each other. In this case, a spring chamber 57 is formed between the piston 51 and the metal spring press member 53, the insulating ring 54 and the metal case 55 of the cylinder, and a metal spring 58 is put in this chamber 57. The metal spring press member 53 and the bellofram press member 56 are provided with terminals 59, 60 and lead pieces 61, 62, respectively, and the resonance coil 30 and the capacitor C of the resonator 5 are connected to these lead pieces 61, 62 and integrally assembled. The bellofram press member 56 is bored with a hole at the center so as to form an air path 63 and the air path 63 is communicated to the valve 25 through the air pipe 27 and the cap nut 26 as shown in FIG. 8.

When the internal pressure of the tire is normal, the pressure is transmitted to the bellofram 50 through the valve 25, the cap nut 26, the air pipe 27 and the air path 63, thereby pressing the piston 51 against force of the metal spring 58, and then the contact ring 52 provided in the flange portion 51' of the piston 51 is made into contact with an extension 55' of the metal case 55. The resonator 5 is then closed through the lead piece 61, the terminal 59, the metal spring press member 53 made of metal, the metal spring 58, the contact ring 52, the metal case 55, the bellofram press member 56, the terminal 60 and the lead piece 62.

When the internal pressure of the tire is abnormal, i.e., the internal pressure is reduced, the bellofram 50 and the piston 51 are pushed back to the bellofram press member 56 against force of the metal spring 58 as shown in FIG. 12, so that the extension 55' of the metal case 55 is separated from the metal contact ring 52 and the resonator 5 is opened.

The invention is not limited to the above described embodiments but can be modified variously. For example, as a means for detecting change of the oscillation condition of the oscillator, use may be made of a frequency detection means. In this case, the detector 7 is used as a frequency detector, and the comparator must be constructed to generate output pulses in case of changing the frequency.

What is claimed is:

1. An alarm device for informing reduction of pneumatic pressure of a tire by converting an abnormal change of the pneumatic pressure into an electric signal and generating an alarm, the device comprising:

at least one oscillator means having an oscillation coil fixed on a chassis side of a vehicle and changing its oscillation state of electromagnetic waves in accordance with an abnormal change of the pneumatic pressure;

a resonator means fixed to the peripheral portion of a wheel having a tire adjacent the oscillation coil and consisting of a resonance coil and a capacitor capable of resonating with the electromagnetic wave radiated from said oscillation coil and a pressure sensing switch for sensing an abnormal change of the pneumatic pressure;

a signal processing device provided for each oscillator and including a detector means for detecting the output of the oscillator, a comparator means for comparing the present output of the detector with a preceding output of the detector to generate an output pulse, an integrator means for integrating the output pulse of the comparator, and a logic circuit means for logically operating the output of the integrator; and an alarm means for generating a warning signal in accordance with the output of the signal processing device.

2. An alarm device as claimed in claim 1, wherein said detector is an amplitude detector.

3. An alarm device as claimed in claim 1, wherein said detector is a frequency detector.

4. An alarm device as claimed in claim 1, wherein said oscillator has an oscillation frequency of 20 KHz–10 MHz.

5. An alarm device as claimed in claim 1, wherein said oscillator has preferably an oscillation frequency of 100 KHz–5 MHz.

* * * * *